US006759365B2

(12) United States Patent
Cavalli et al.

(10) Patent No.: US 6,759,365 B2
(45) Date of Patent: Jul. 6, 2004

(54) CATALYSTS FOR OXYCHLORINATION OF ETHYLENE TO 1,2-DICHLOROETHANE

(75) Inventors: Luigi Cavalli, Novara (IT); Francesco Casagrande, Novara (IT)

(73) Assignee: SUD Chemie Mt S.r.l., Milan (IT)

( * ) Notice: Subject to any disclaimer, the term of this patent is extended or adjusted under 35 U.S.C. 154(b) by 0 days.

(21) Appl. No.: 10/277,466

(22) Filed: Oct. 22, 2002

(65) Prior Publication Data

US 2003/0096700 A1 May 22, 2003

(30) Foreign Application Priority Data

Oct. 25, 2001 (IT) .................................... MI2001A2241

(51) Int. Cl.[7] .............................................. B01J 23/70
(52) U.S. Cl. ....................... 502/346; 502/341; 570/224
(58) Field of Search ............................... 502/340, 341, 502/345, 346; 570/224

(56) References Cited

U.S. PATENT DOCUMENTS

| 3,360,483 A | 12/1967 | Diamond et al. |
| 4,587,230 A | 5/1986 | Cavaterra et al. |
| 5,192,733 A | 3/1993 | Mainz et al. |
| 5,315,051 A | 5/1994 | Derleth et al. |
| 5,527,754 A | 6/1996 | Derleth et al. |

FOREIGN PATENT DOCUMENTS

| EP | 0 176 432 | 4/1986 |
| EP | 0 375 202 | 6/1990 |
| EP | 0 494 474 | 7/1992 |

*Primary Examiner*—Stanley S. Silverman
*Assistant Examiner*—Edward M. Johnson
(74) *Attorney, Agent, or Firm*—Welsh & Katz, Ltd.

(57) ABSTRACT

Catalysts for the oxychlorination of ethylene to 1,2-dichloroethylene, comprising compounds of Cu and Mg supported on alumina, in which the copper content, expressed as Cu, is 2 to 8% by weight, the Mg/Cu atomic ratio is from 1.2 to 2.5, and the specific surface of the catalyst is from 30 to 130 $m^2/g$.

8 Claims, No Drawings

CATALYSTS FOR OXYCHLORINATION OF ETHYLENE TO 1,2-DICHLOROETHANE

FIELD OF THE INVENTION

The present invention relates to catalysts for the oxychlorination of ethylene to dichloroethane (DCE) capable of providing high conversion rates without sacrificing selectivity by working in a fluid bed at high temperatures, and to the process in which the catalysts are used.

BACKGROUND OF THE INVENTION

Dichloroethane is an important intermediate product for the production of vinyl chloride and therefore of PVC, one of the most widely used plastic materials.

Various technologies are used in the oxychlorination reaction. The reactors can be of the fixed- or fluid-bed type, and air and/or oxygen can be used as oxidizer.

The fluid-bed process is preferred over the fixed-bed process because it offers several advantages: lower investment costs for the reactors (because they are not made of steel), an almost isothermal thermal profile without hot spots (therefore with high selectivity and limited ageing phenomena).

Fluid-bed processes use catalysts based on copper salts, preferably $CuCl_2$, mixed with various promoters, such as salts of alkaline metals, alkaline earth metals, and rare earths. The supports are based on alumina or various aluminum silicates (attapulgite, montmorillonite, silica gels, clays, et cetera); alumina having a particle size suitable for good fluidization is generally preferred.

Catalysts must provide the following performance:

ensure the highest possible yield of dichloroethane by virtue of satisfactory selectivity and high activity (high conversion rates of the hydrochloric acid);

be able to work with good fluidization conditions, avoiding sticking (sticking of the particles, due to a polymeric form of $CuCl_2$ with a low melting point); sticking can be avoided by reducing the ratio between HCl and ethylene, but clearly this inevitably reduces the dichloroethane yield;

avoid losses of active elements and promoters, which in addition to penalizing the catalytic activity are a problem for the pollution of the process effluent-water;

provide high flexibility, in that production can be adapted to high market demand; in this case it is necessary to have catalysts capable of working at higher temperatures without sacrificing selectivity and without an increased loss of active element and promoter.

Currently, the most competitive fluid-bed process is the one that uses oxygen as oxidizer: in such conditions, the reaction is performed with partial conversion and therefore with recycling of the unconverted ethylene and of the carbon oxides that are by-products in the oxychlorination reaction. This technology has some important advantages: conversion of the hydrochloric acid is substantially complete; the efficiency of the ethylene is on average higher that that obtained in the process in air (because the ethylene is fully converted); the emission of incondensable gases into the atmosphere (venting) is reduced drastically, since it is not necessary to eliminate from the cycle, as in the case of the air process, the nitrogen supplied together with the air.

This aspect is particularly important for environmental impact, thanks to the low emission of noxious chlorinated compounds into the environment; the vented output can be sent into the atmosphere without further expensive treatments. Another advantage is the elimination, with respect to the air process, of the section for absorbing and stripping the dichloroethane contained in the gases that leave the system.

An important parameter that can affect the yield of the reaction is the molar ratio of $HCl/C_2H_4$ in the mixture of the reacting gases entering the reactor: this ratio is not stoichiometric (2), but is close to the stoichiometric value in the air process (1.9–1.96) and is between 1.7 and 1.9 in the oxygen process since the concentration of the ethylene also comprises the ethylene that is fed back to the reactor with the recirculation gas.

In the air process, with high $HCl/C_2H_4$ ratios, selectivity is generally high, but the limit is represented by the conversion of the hydrochloric acid and by defluidization.

In the oxygen process with lower $HCl/C_2H_4$ molar ratios, conversion of the hydrochloric acid is facilitated, but unfortunately reactions of combustion to carbon oxides are also facilitated, and this leads to a loss of selectivity and therefore to a higher specific consumption of ethylene.

In order to compensate for this aspect, the temperature of the fluid bed is usually kept low (210–225° C.): in this manner, the final yield of the reaction is higher than 98% molar (moles of DCE produced with respect to moles of ethylene fed). The specific productivity of the system is low.

This fact is in contrast with the current trend of technology: the DCE producer tends to increase the specific productivity of the system without resorting to onerous investments for new reactors. To do so, the flow-rate of reagents in input to the reactor is increased, consequently reducing the conversion of the reagents (especially of hydrochloric acid), and this entails a reduction in the yield of the process but also entails severe corrosion problems arising from the unconverted hydrochloric acid. To overcome this problem, the temperature of the fluid bed is increased, but this causes an increase in the combustion reactions and in forming of unwanted chlorinated byproducts, which is not compensated by the decrease in residence time.

Therefore, in the field there is the strongly felt need to have an oxychlorination catalyst that is capable of providing high selectivities at high temperatures (>230° C.) both in the oxygen process and in the air process.

Various patents published in patent literature disclose catalysts that have high selectivities at high temperatures.

For example, application EP-A-582165 discloses a catalyst based on copper salts that comprises various promoters (salts of Mg, K and rare earths). The synergistic action of three promoters allegedly allows to obtain good selectivities.

The maximum working temperature is 240° C.; the selectivity of ethylene to pure dichloroethane is 94.98% molar; the selectivity to combustion products is 3.86% molar. Selectivity to triane (1,1,2-trichloroethane, the most important chlorinated byproduct) is 0.71%. Catalytic tests are conducted in the conditions of the air process; no information is given regarding the oxygen process. The support impregnation method is "wetted" (i.e., the method of dry impregnation by using a volume of solution that is equal to, or smaller than, the porosity of the substrate is not used).

U.S. Pat. No. 5,227,548 discloses a catalyst that comprises cupric chloride and chlorides of Mg and K, which have the synergistic effect of reducing the combustion of ethylene to CO and $CO_2$. The method of preparation used in the examples is wet impregnation; a catalyst with an Mg/Cu ratio of 0.3 is used.

U.S. Pat. No. 5,527,734 discloses a catalyst that comprises cupric chloride and chlorides of Mg and Cs supported on gamma alumina, in which the atomic ration of Mg/Cu is at least 0.3 and can reach 2.6, but preferably does not exceed 1.5 and more preferably 1.

The combined use of Mg and Cs chlorides is necessary to avoid dirtying the surface of the tubes used to cool the fluid bed.

The Cu content of the catalyst is preferably 5–6% by weight. This content is high: it facilitates sticking and unwanted reactions (combustions and abundant forming of 1,1,2-trichloroethane; the catalyst is prepared with the dry impregnation method, but without using acid solutions (for hydrochloric acid or other acids).

U.S. Pat. No. 4,587,230 discloses a catalyst that comprises cupric chloride and Mg chloride in an Mg/Cu ratio of 0.2–1.1, in which the Cu atoms are arranged more inside the particle of the catalyst than at its surface (the X/Y ratio, where X=Al/Cu in the catalyst and Y=Al/Cu at the surface is at least 1.4).

Preparation is performed by dry impregnation, by using acid solutions of salts of Cu and Mg for hydrochloric acids or other acids in a quantity of 1 equivalent per g-atom of Cu or by treating a catalyst that contains Cu of the commercial type with an acid solution of Mg chloride.

The Mg/Cu ratio is preferably 0.5–0.8:1.

The catalyst has good selectivity to DCE up to temperatures of 230° C.

BRIEF DESCRIPTION OF THE INVENTION

It has now been found surprisingly that it is possible to obtain catalysts for the fluid-bed oxychlorination of ethylene to 1,2-dichloroethane (DCE) that are capable of providing a better performance (particularly selectivity at high temperatures) than hitherto known catalysts.

The catalysts according to the invention comprise a copper compound, preferably cupric chloride, in an amount expressed as Cu from 2 to 8% by is weight, and a magnesium compound, preferably the chloride, supported on alumina, and are characterized by:

an atomic ratio of Mg/Cu equal to, or greater than, 1.2, preferably between 1.3 and 2.5;

a distribution of the copper atoms more inside the particle of the catalyst than at the surface (layer of 20–30 Å) and a higher distribution of the magnesium atoms at the surface (layer of 20–30 Å) than inside the particle;

a specific surface of the catalyst of 30 to 130 m$^2$/g, preferably 70 to 100 m$^2$/g.

Moreover, it has been found that the use of gamma alumina containing less than 50 ppm of impurities derived from sodium compounds (expressed as Na), preferably less than 10 ppm, provides catalysts that are more stable (less crumbly), have high abrasion resistance, do not produce during reaction fines that would be lost through the cyclone separators and/or might deposit on the bed cooling tubes, thus hindering the heat exchange and accordingly the control of the reaction.

DETAILED DESCRIPTION OF THE INVENTION

As already noted, the catalysts allow to work at very high temperatures, preferably higher than 235° C., particularly between 240 and 265° C., without compromising the DCE selectivity of the catalyst. The greater heat exchange that can be provided at higher temperatures than those normally used allows to increase considerably the productivity of the system. For an equal productivity, the surface of the cooling tubes that is used is smaller and therefore the reactor is smaller. The higher activity of the catalyst that can be obtained at high temperatures without however compromising DCE selectivity allows to use less catalyst.

Moreover, the catalysts allow to:

avoid sticking, also by working with high Cl/C molar ratios, and losses of active component and promoter in industrial use;

reduce the loss of fines through the cyclone separators and of copper compound during operation;

increase the production of dichloroethane by increasing the total flow-rate of the reagents without modifying the reactor.

The catalysts are prepared with the method of dry impregnation, i.e., by using a volume of solution that is equal to, or smaller than, the porosity of the substrate.

Acid solutions for hydrochloric acid and/or other strong acids in quantities preferably equal to 1–2 equivalents per g-atom of Cu are used.

The solution is sprayed onto the alumina placed in a container that is kept under rotation or also by working in a fluid bed.

After impregnation, the catalyst is dried for example at 130° C. for one night.

The salts used are preferable chlorides, but it is also possible to use other salts, such as nitrates and carbonates, so long as they are soluble.

Determination of the distribution of copper and magnesium is performed with the XPS (X-ray Photoemission Spectroscopy) method. This method measures the surface concentration (layer of 20–30 Å) of the atoms of Cu and Mg, i.e., the surface ratio of Al/Cu and Al/Mg.

For further information on this method, reference is made to U.S. Pat. Nos. 4,587,230 and 4,871,707.

In particular, in the catalysts according to the present invention the ratios X=Al/Cu at the surface and Y=Al/Cu within the catalyst are such that X/Y is greater than 1.2 and can reach 2.7 (for an atomic ratio of Mg/Cu of 2); the ratios Al/Mg=Z at the surface and V=Al/Mg within the catalyst are such that V/Z is between 1.5 and 3. In particular, for Cu contents of approximately 4% by weight and Mg contents of 2.1 to 2.3% by weight and for Mg/Cu ratios of 1.3 and 1.4, the ratio X/Y is 1.4 and 1.6.

The content of copper compound expressed as Cu of the catalyst is preferably 4–5% by weight.

The alumina used as a support has a surface area of 80 to 200 m$^2$/g and is chosen so that the catalyst has an area of 60 to 110 m$^2$/g. The volume of the pores is 0.4–0.5 g/ml; the particle size distribution is preferably such that in the catalysts the fraction under 40 microns is between 50 and 80% by weight, with substantial exclusion of fractions under 20 microns.

The following examples are provided by way of non-limitative illustration of the scope of the invention.

Description of the Catalyst Preparation Method

The various catalysts are prepared by using a gamma alumina with specific characteristics, such as surface area (80–200 m$^2$/g), pore volume (0.4–0.5 ml/g), purity (Na<2 ppm, Fe<15 ppm) and particle size distribution as defined in the tables. This alumina is weighed and then impregnated with a volume of solution that contains the copper salt and the promoters, which corresponds to approximately 90% of the pore volume. The salts used are generally copper chloride ($CuCl_2*2H_2O$) and magnesium chloride ($MgCl_2*6H_2O$). HCl, in an amount of 2.5 g (HCl 37% by weight) for 100 g of alumina is added to the solution.

The salt solution is prepared by dissolving said salts in distilled water and by facilitating the dissolution with bland heating; then the solution is sprayed onto the alumina placed in a cylindrical jar (capacity 10 l, made of glass or quartz) kept under rotation by a trundler. The operation is performed slowly, so as to facilitate complete homogenization.

After impregnation, the catalyst is dried at 130° C. for one night and is then loaded into the reactor.

The salts used are generally chlorides, but it is possible to use other salts such as nitrates, carbonates and the like, so long as they are soluble.

Impregnation can be performed in a cylindrical container or also in a fluid bed.

The catalysts thus prepared were characterized chemically and physically; their characteristics are listed in Table 1. Moreover, determinations with the XPS method were performed in order to verify the distribution of copper and of magnesium.

Description of the Apparatus Used for Catalytic Tests

The apparatus used to determine the performance of the various catalysts is constituted by a glass reactor, a system for the controlled feeding and dosage of the reagents, a cooling system for condensing and recovering the condensable products (DCE, $H_2O$ containing HCl, chlorinated byproducts). The incondensable products ($N_2$, $O_2$, CO, $CO_2$, Ar) are measured, analyzed by gas chromatography and released into the atmosphere. During the test (which lasts one hour), the condensed products are collected in two phases, an aqueous one and an organic one. The two phases are separated and weighed: the unconverted hydrochloric acid is determined in the aqueous phase by acidimetric titration, and the organic phase is analyzed by gas chromatography in order to determine the purity of the DCE and to verify the quantity of chlorinated byproducts formed (with particular reference to 1,1,2-trichloroethane). As mentioned, the incondensable gases are measured and analyzed by gas chromatography in order to determine $C_2H_4$, $CO_2$, CO, $O_2$ and $N_2$. In this manner it is possible to obtain a complete balance and to determine the performance of a catalyst, such as the conversion of hydrochloric acid and ethylene, the selectivity of ethylene and hydrochloric acid to DCE, and the purity of DCE.

The dimensions of the reactor are: inside diameter 37 mm, height 300 cm.

The tests were conducted under pressure (4 ata), with a linear velocity of 9–11 cm/s, and at working temperatures between 220 and 265° C. Tests with air as oxidizer were conducted with a Cl/C molar ratio of 0.97–0.99 and of 0.88–0.92 with $O_2$ (process with recycling).

The pilot reactor is capable of providing a performance that can be extrapolated to an industrial reactor.

EXAMPLE 1

A catalyst with a 4.15% content of Cu and a 2.12% content of Mg is prepared according to the method described above. The Mg/Cu ratio is 1.336.

The support used (the same for all the catalysts of the comparison examples) has the following characteristics:
surface area: 180 $m^2/g$;
pore volume: 0.45 ml/g;
fraction of particles between 63 and 40 $\mu m$: 40% by weight
fraction of particles smaller than 40 $\mu m$: 32%.

The characteristics of the catalyst are summarized in Table 1, which also lists the data related to the catalysts of examples 2 and 3 and of comparison examples 1 and 2. The table also reports the values related to the distribution of the atoms of Cu and Mg determined with XPS, which shows that as the Mg/Cu ratio increases, the distribution of copper (which in any case is distributed preferentially inside the particle) inside the particle rather than on the surface is less favored and that the magnesium, differently from the Cu, is distributed more preferentially on the surface).

All the catalysts are tested in a pilot plant under the following conditions:
Cl/C=0.89–0.9
$O_2/C_2$=0.53–0.56
Pressure=4 ata
Contact time=18–20 s
Linear velocity=10 cm/s The reaction conditions are typical of the oxygen process: they are kept as constant as possible during the tests with the various catalysts in order to have meaningful comparisons.

The results of the various tests, conducted at three temperatures (235, 245 and 255° C.), are listed in Table 2. The positive effect of the increase in the Mg/Cu ratio is evident: the conversion of the hydrochloric acid increases, DCE selectivity improves due to the decrease in the combustion reactions and in the forming of chlorinated byproducts: in this manner it is possible to work at a higher temperature without sacrificing selectivity.

Further improvements have been achieved with the catalysts of example 2 and 3.

1. The catalyst of example 2 was prepared with the same support as the catalysts of example 1 and of comparison examples 1 and 2, with the difference that the surface area was decreased to 83 $m^2/g$.
2. The catalyst of example 3 was prepared with a support having a different particle size, in which the fraction smaller than 40 $\mu m$ was 59% by weight.

The results, also listed in Table 2, indicate that the two variations further improved performance.

Comparison Examples 1 and 2

The catalysts are prepared and tested as in example 1, the only difference being that the Mg/Cu ratio is 0.676 in comparison example 1 and 0.988 in comparison example 2 (see Table 1 for the chemical, physical and particle size characteristics and Table 2 for the results of the catalytic tests).

EXAMPLES 2 and 3

The catalysts are prepared and tested as in example 1; the only difference is that the Mg/Cu ratio is 1.402 in example 2 and 1.391 in example 3, and that the fraction of the particles smaller than 40 microns was 59% by weight in the catalyst of example 3 and that the surface area in the two catalysts is respectively 83 and 98.7 $m^2/g$ (the surface area in the two supports was 150 $m^2/g$).

The catalyst of example 3 was also compared with the catalyst of example 1. The tests were conducted in the conditions of the air process, working with a Cl/C molar ratio of 0.97–0.99. The results of the tests confirm the positive effect of the fraction smaller than 40 microns. The fluid-dynamics behavior of the catalyst was found to be satisfactory: no sticking was noted.

The disclosure in Italian Patent Application No. MI2001A002241 from which this application claims priority are incorporated herein by reference.

TABLE 1

CHEMICAL COMPOSITION AND PHYSICAL CHARACTERISTICS OF THE CATALYSTS

| CATALYSTS | | Comparison 1 | Comparison 2 | Example 1 | Example 2 | Example 3 |
|---|---|---|---|---|---|---|
| CHEMICAL COMPOSITION | | | | | | |
| Cu | % W | 3.92 | 4.10 | 4.15 | 4.29 | 4.33 |
| Mg | " | 1.013 | 1.55 | 2.12 | 2.3 | 2.30 |
| Mg/Cu | Atomic ratio | 0.676 | 0.988 | 1.336 | 1.402 | 1.391 |
| SURFACE COMPOSITION (XPS) | | | | | | |
| Al/Cu bulk (Y) | Atomic ratio | 27.05 | 25.12 | 24.13 | 23.06 | 22.82 |
| Al/Cu XPS (X) | " | 52.4 | 53 | 38.8 | 33.4 | 38.47 |
| X/Y | | 1.94 | 2.11 | 1.61 | 1.45 | 1.69 |
| Al/Mg bulk (V) | Atomic ratio | 43.83 | 25.41 | 18.07 | 16.45 | 16.40 |
| Al/Mg XPS (Z) | " | 9.73 | 9.14 | 7.00 | 6.68 | 8.83 |
| Z/V | | 0.22 | 0.36 | 0.39 | 0.41 | 0.54 |
| V/Z | | 4.50 | 2.78 | 2.58 | 2.46 | 1.86 |
| PHYSICAL CHARACTERISTICS | | | | | | |
| Surface area | $m^2/g$ | 130 | 125 | 123 | 83 | 98.7 |
| Apparent densit | g/ml | 1.58 | 1.6 | 1.79 | 1.76 | 1.77 |
| Actual density | " | 3.19 | 3.15 | 2.85 | 2.75 | 2.77 |
| Pore volume | ml/g | 0.32 | 0.308 | 0.21 | 0.20 | 0.20 |
| Average radius | Å | 49.1 | 49.2 | 33.79 | 49.29 | 40.53 |
| PARTICLE DISTRIBUTION | | | | | | |
| >125 | $\mu$ | 0.8 | 0.6 | 0.5 | 1 | 0.3 |
| 125–90 | " | 4.5 | 5.0 | 3.5 | 5.8 | 1.4 |
| 90–63 | " | 19.2 | 23.8 | 21.5 | 23.2 | 4.6 |
| 63–40 | " | 37.2 | 41.7 | 45.1 | 38.4 | 31.5 |
| <40 | " | 38.3 | 28.9 | 29.4 | 31.6 | 59 |
| <20 | " | 0.0 | 0.0 | 0.0 | 0.0 | 3.2 |

TABLE 2

CONSTANT CONDITIONS OF THE TESTS

| | |
|---|---|
| Pressure (ata) | 4 |
| Cl/C, molar ratio | 0.89–0.9 |
| $O_2$/C, molar ratio | 0.53–0.56 |
| Contact time (s) | 18–20 |
| Linear velocity (cm/s) | 10 |
| TEMPERATURE ° C. | 235 |

| CATALYST | CONVERSION % HCl | SELECTIVITY Molar % of $C_2H_4$ to DCE | SELECTIVITY Molar % of $C_2H_4$ to $CO_x$ | SELECTIVITY Molar % of $C_2H_4$ to TRI-ANE | DCE PURITY Molar % | YIELD % Molar $C_2H_4$ to DCE |
|---|---|---|---|---|---|---|
| Comparison Ex. 1 | 99.76 | 94.6 | 4.81 | 0.221 | 99.42 | 94.5 |
| Comparison Ex. 2 | 99.64 | 95.7 | 3.79 | 0.219 | 99.53 | 95.6 |
| Example 1 | 99.78 | 96.6 | 2.93 | 0.208 | 99.53 | 96.5 |
| Example 2 | 99.01 | 98.1 | 1.01 | 0.164 | 99.56 | 98.0 |

TEMPERATURE ° C. 245

| CATALYST | CONVERSION % HCl | SELECTIVITY Molar % of $C_2H_4$ to DCE | SELECTIVITY Molar % of $C_2H_4$ to $CO_x$ | SELECTIVITY Molar % of $C_2H_4$ to TRI-ANE | DCE PURITY Molar % | YIELD % $C_2H_4$ to DCE |
|---|---|---|---|---|---|---|
| Comparison Ex. 1 | 99.4 | 94.2 | 5.09 | 0.298 | 99.29 | 94.1 |
| Comparison Ex. 2 | 99.4 | 94.7 | 4.68 | 0.278 | 99.33 | 94.6 |
| Example 1 | 99.6 | 95.6 | 3.76 | 0.287 | 99.35 | 95.5 |
| Example 2 | 99.3 | 97.0 | 2.43 | 0.285 | 99.38 | 96.9 |
| Example 3 | 99.2 | 97.6 | 1.81 | 0.26 | 99.39 | 97.5 |

TEMPERATURE ° C. 255

| CATALYST | CONVERSION % HCl | SELECTIVITY Molar % of $C_2D_4$ to DCE | SELECTIVITY Molar % of $C_2D_4$ to $CO_x$ | SELECTIVITY Molar % of $C_2D_4$ to TRI-ANE | DCE PURITY Molar % | YIELD % Molar $C_2H_4$ to DCE |
|---|---|---|---|---|---|---|
| Comparison Ex. 1 | 97.7 | 93.6 | 5.52 | 0.428 | 99.04 | 93.5 |
| Comparison Ex. 2 | 98.9 | 94.6 | 4.49 | 0.375 | 99.20 | 94.5 |
| Example 1 | 99.0 | 94.6 | 4.76 | 0.373 | 99.29 | 94.5 |
| Example 2 | 98.9 | 96.5 | 2.80 | 0.368 | 99.26 | 96.4 |
| Example 3 | 98.9 | 96.66 | 2.70 | 0.320 | 99.35 | 96.6 |

What is claimed is:

1. Catalysts for the oxychlorination of ethylene to 1,2-dichloroethane, comprising compounds of Cu and Mg supported on alumina and having a copper content, expressed as Cu, of 2 to 8% by weight, wherein the Mg/Cu atomic ratio is from 1.2 to 2.5, with distribution of the copper atoms more inside the particle of the catalyst than on the surface (layer with a thickness of 20–30 Å) and of the magnesium atoms more on the surface (20–30 Å layer) than inside the particle, and in that the specific surface of the catalyst is from 30 to 130 $m^2$/g.

2. The catalysts according to claim 1, wherein the Mg/Cu ratio is from 1.3 to 2 and the distribution of the copper atoms is such that the X/Y ratio is from 1.2 to 2.7 (X is the Al/Cu ratio at the surface and Y is the Al/Cu ratio within the particle of the catalyst) and the distribution of the magnesium atoms is such that the V/Z ratio is from 1.5 to 3 (V is the Al/Mg ratio within the particle of the catalyst, Z is the Al/Mg ratio at the surface).

3. The catalysts according to claim 1, wherein the specific surface of the catalyst is 70–100 $m^2$/g.

4. The catalyst according to claim 1, wherein the particle size distribution of the catalyst is such that the fraction smaller than 40 microns is from 50 to 80% by weight and the fraction smaller than 20 microns is practically absent.

5. The catalysts according to claim 1, wherein the copper compound is cupric chloride and the magnesium compound is magnesium chloride.

6. The catalysts according to claim 1, wherein the support is gamma alumina with a purity such that the impurity content (expressed as Na) is less than 10 ppm.

7. A process for preparing dichloroethane by fluid-bed oxychlorination of ethylene by using air and/or oxygen as oxidizers and $HCl/C_2H_4$ molar ratios in the mixture of the reacting gases entering the reactor of 1.9–19.6 when using air and of 1.7–1.9 when using oxygen and by working at reaction temperatures between 235 and 265° C., wherein the oxychlorination is carried out in the presence of a catalyst as defined in claim 1.

8. A method for preparing a catalyst as defined in claim 1, wherein alumina is impregnated with aqueous solutions of Cu and Mg salts that are acid by hydrochloric acid or other strong acids, using a volume of solution that is equal to, or smaller than, the porosity of the alumina.

* * * * *